(12) United States Patent
Benchikh et al.

(10) Patent No.: US 10,253,006 B2
(45) Date of Patent: Apr. 9, 2019

(54) ASSAY FOR THE DETECTION OF THE PHENYLPIPERAZINE FAMILY

(71) Applicant: RANDOX LABORATORIES LIMITED, Crumlin, Antrim (GB)

(72) Inventors: Elouard Benchikh, Crumlin (GB); Ivan McConnell, Crumlin (GB); Philip Lowry, Crumlin (GB); Peter Fitzgerald, Crumlin (GB)

(73) Assignee: Randox Laboratories Limited (GB)

(*) Notice: Subject to any disclaimer, the term of this patent is extended or adjusted under 35 U.S.C. 154(b) by 211 days.

(21) Appl. No.: 15/130,137

(22) Filed: Apr. 15, 2016

(65) Prior Publication Data

US 2016/0229824 A1 Aug. 11, 2016

Related U.S. Application Data

(63) Continuation of application No. 13/774,518, filed on Feb. 22, 2013, now abandoned.

(30) Foreign Application Priority Data

Feb. 24, 2012 (GB) .................................... 1203266

(51) Int. Cl.
| | |
|---|---|
| C07D 295/155 | (2006.01) |
| G01N 33/53 | (2006.01) |
| C07K 14/47 | (2006.01) |
| C07K 14/765 | (2006.01) |
| C07K 16/44 | (2006.01) |
| C07D 295/096 | (2006.01) |
| C07D 241/04 | (2006.01) |

(52) U.S. Cl.
CPC ....... *C07D 295/155* (2013.01); *C07D 241/04* (2013.01); *C07D 295/096* (2013.01); *C07K 14/47* (2013.01); *C07K 14/765* (2013.01); *C07K 16/44* (2013.01); *G01N 33/5308* (2013.01); *C07K 2317/76* (2013.01)

(58) Field of Classification Search
CPC .............. C07D 241/04; C07D 295/096; C07D 295/155; C07K 14/47; C07K 14/765; C07K 16/44; C07K 2317/76; G01N 33/5308

See application file for complete search history.

(56) References Cited

U.S. PATENT DOCUMENTS

| | | |
|---|---|---|
| 8,476,029 B2 | 7/2013 | Benchikh et al. |
| 2007/0259846 A1 | 11/2007 | Hoenke et al. |

FOREIGN PATENT DOCUMENTS

| | | |
|---|---|---|
| EP | 2261259 A1 | 12/2010 |
| WO | WO 2010/142974 | * 12/2010 |

OTHER PUBLICATIONS

Goldsby et al., "Immunology," W.H. Freeman & Co., N.Y., 2003, p. 69.*
Englebienne, "Immune and Receptor Assays in Theory and Practice," CRC Press, 2000, p. 308.*
Consiglio et al., "Characterization of phosphate residues on thyroglobulin," J. Biol. Chem., 1987, vol. 262, No. 21, pp. 10304-10314.*
Goodrow et al., "Strategies for Immunoassay Hapten Design," in Immunoanalysis of Agrochemicals; Nelson, J., et al.; ACS Symposium Series, 1995, vol. 586, Chapter 9, pp. 119-139.*
Antia U, Tingle M, Russel B. Validation of an LC-MS Method for the Detection and Quantification of BZP and TFMPP and their Hydroxylated Metabolites in Human Plasma and its Application to the Pharmacokinetic Study of TFMPP in Humans. J Forensic Sci, Sep. 2010;55(5):1311-1318.
Baumann M, Clark R, Budzynski A, Partilla J, Blough B, Rothman RB. N-Substituted Piperazines Abused by Humans Mimic the Molecular Mechanism of 3,4-Methylenedioxymethamphetamine (MDMA, or 'Ecstasy'). Neuropsychopharmacology, 2005;30:550-560.
Microgram Bulletin. The Drug Enforcement Administration, May 2009;42(5):45-52. http://www.justice.gov/dea/pr/micrograms/2009/mg0509.pdf.
BZP and other piperazines. EMCDDA. http://www.emcdda.europa.eu/publications/drug-profiles/bzp, Feb. 21, 2013.
Fitzgerald, S, Lamont J, McConnell R, Benchikh. Development of a High-Throughput Automated Analyzer Using Biochip Array Technology. Clinical Chemistry, 2005;51(7):1165-1176.
Logan B, Costantino A, Rieders E, Sanders D. Trazodone, meta-Chlorophenylpiperazine (an Hallucinogenic Drug and Trazodone Metabolite), and the Hallucinogen Trifluoromethylphenylpiperazine Cross-React with the EMIT II Ecstasy Immunoassay in Urine. Journal of Analytical Toxicology 2010;34:587-589.
Maurer H, Kraemer T, Springer D, Staack R. Chemistry, Pharmacology, Toxicology, and Hepatic Metabolism of Designer Drugs of the Amphetamine (Ecstasy), Piperazine, and Pyrrolidinophenone Types, A Synopsis. Ther Drug Monit, Apr. 2004;26(2):127-131.
Nikolova L, Danchev N. Piperazine Based Substances of Abuse: A New Party Pills on Bulgarian Drug Market. Biotechnol. & Biotechnol. EQ, 2008;22:652-655.

(Continued)

*Primary Examiner* — Galina Yakovleva (74) *Attorney, Agent, or Firm* — Womble Bond Dickinson (US) LLP (57) ABSTRACT

The current invention describes novel immunogens which are used in the production of novel antibodies with unique binding properties in that they cross-react with a variety of phenylpiperazine derivatives. These antibodies enable methods and kits to detect and/or determine phenylpiperazine derivatives (for example mCPP, TFMPP and MeOPP) in an in vitro sample which are advantageous over currently available analytical methods in terms of cost, ease of use, speed and sensitivity.

13 Claims, 3 Drawing Sheets

(56) References Cited

OTHER PUBLICATIONS

Peters F, Martinez-Ramirez, J. Analytical Toxicology of Emerging Drugs of Abuse. Ther Drug Monit, 2010;32:532-539.
Staack R, Maurer H. Piperazine-Derived Designer Drug 1-(3-Chlorophenyl)piperazine (mCPP): GC-MS Studies on its Metabolism and its Toxicological Detection in Rat Urine Including Analytical Differentiation from its Precursor Drugs Trazodone and Nefazodone. Journal of Analytical Toxicology, 2003;27:560-568.
Staack R, Fritschi G, Maurer H. New designer drug 1-(3-trifluoromethylphenyl)piperazine (TFMPP): gas chromatography/mass spectrometry and liquid chromatography/mass spectrometry studies on its phase I and II metabolism and on its toxicological detection in rat urine. J Mass Spectrum, 2003;38:971-981.
Beckman Coulter "EMIT(R) II Plus Ecstasy Assay," Feb. 2013.

\* cited by examiner

| Name (acronym) | R1 | R2 | R3 | R4 |
|---|---|---|---|---|
| 1-(3-Chlorophenyl)-4-(3-chloropropyl) piperazine (*mCPCPP*) | H | Cl | H | -(CH$_2$)$_3$-Cl |
| 1-(3-Chlorophenyl) piperazine (*mCPP*) | H | Cl | H | H |
| 1-(4-Chlorophenyl) piperazine (*pCPP*) | H | H | Cl | H |
| 1-(4-Fluorophenyl) piperazine (*pFPP*) | H | H | F | H |
| 1-(2-Methoxyphenyl) piperazine (*oMeOPP*) | MeO | H | H | H |
| 1-(4-Methoxyphenyl) piperazine (*pMeOPP*) | H | H | MeO | H |
| 1-(3-Methylphenyl) piperazine (*mMPP*) | H | Methyl | H | H |
| 1-(4-Methylphenyl) piperazine (*pMPP*) | H | H | Methyl | H |
| 1-(3-Trifluoromethylphenyl) piperazine (*mTFMPP*) | H | CF$_3$ | H | H |

Figure 1

Hapten - A

Hapten - B

Figure 2

Figure 3

ASSAY FOR THE DETECTION OF THE PHENYLPIPERAZINE FAMILY

RELATED APPLICATIONS

This application is a continuation application of U.S. patent application Ser. No. 13/774,518, filed Feb. 22, 2015, of identical title, the entire contents of said application being incorporated by reference herein.

BACKGROUND

Figure 1:
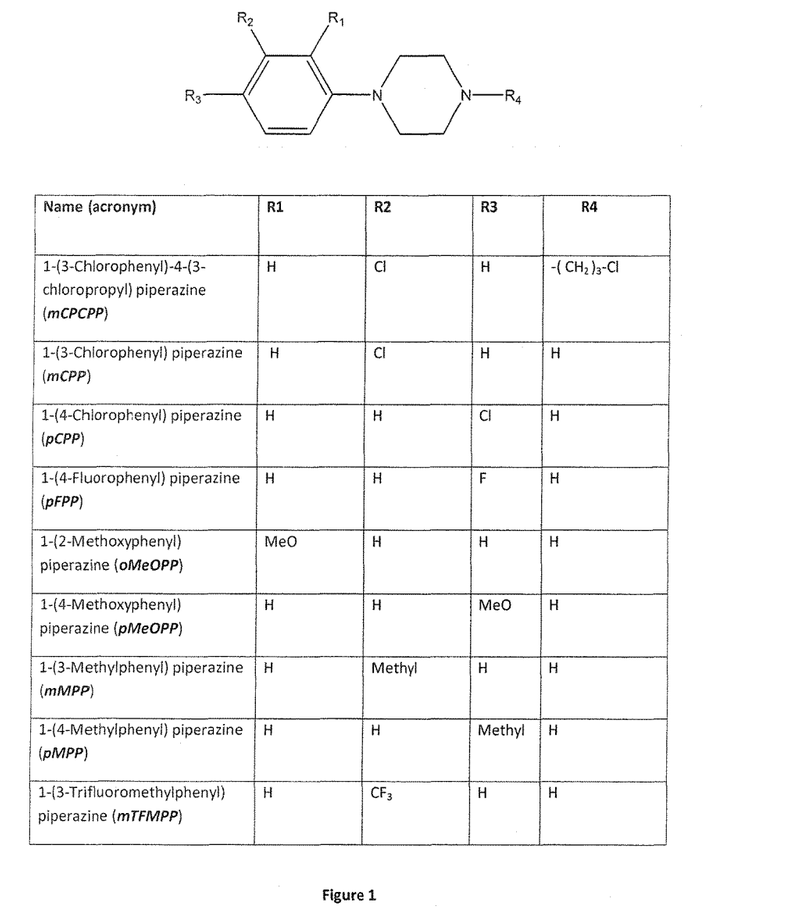
FIG. 1 Structures of phenylpiperazine derivatives
FIG. 2 Structures of haptens A and B
FIG. 3 Preparation of hapten B

In recent years piperazine derivatives have emerged as a new class of designer drugs, gaining popularity especially among young people in the dance music scene where they are commonly known as 'party pills'. They are often marketed as 'natural' or 'herbal' products but are in fact entirely synthetic chemicals. Coupled with their ease of availability and varying legal status across the globe this can create the misconception that these drugs are safe and without the risks commonly associated with traditional street drugs. Piperazine derivatives are usually found in illicit dosage forms as either tablets or capsules, but loose powders and more rarely solutions also occur. The tablets often carry logos similar to those seen on ecstasy tablets and they are often misleadingly sold as ecstasy or as apparent 'safer' and 'legal' alternatives. Their name derives from the piperazine heterocycle which is a common feature and they can be divided into two subclasses; the benzylpiperazines, such as 1-benzylpiperazine (BZP) itself, and the phenylpiperazines which include 1-(3-chlorophenyl)piperazine (mCPP), 1-(4-methoxyphenyl)piperazine (MeOPP) and 1-(3-Trifluoromethylphenyl)piperazine (TFMPP) (FIG. 1 shows the structure of these and other phenylpiperazine derivatives).

The phenylpiperazines are extensively metabolised with the major metabolic reaction being metabolic alteration of the aromatic ring, either by hydroxylation (mCPP, TFMPP) or by O-demethylation of the methoxy moiety (MeOPP) (Maurer et al., 2004). Metabolic degradation of the piperazine moiety to the corresponding ethylenediamine or aniline derivatives is also observed. Metabolic phase II reactions are partial glucuronidation or sulphation of the phenolic metabolites, methylation of the catechols and partial acetylation of the aniline derivatives (Maurer et al., 2004).

One of the most widespread phenylpiperazines, mCPP, is an active metabolite of the antidepressant drug trazodone and related therapeutic drugs. mCPP is a 5-HT receptor agonist with stimulant and hallucinogenic properties similar to 3,4-methylenedioxy-N-methamphetamine (MDMA; the active ingredient of ecstasy), unlike MDMA it does not cause an increase in heart rate or blood pressure. There are two positional isomers of mCPP, 1-(4-chlorophenyl)piperazine and 1-(2-chlorophenyl)piperazine. By 2006, it was estimated that almost 10% of illicit tablets sold in the EU, as part of the illicit ecstasy market, contained mCPP (European Monitoring Centre for Drugs and Drug Addiction, EMCDDA). It has now been suggested from anecdotal reports of users online that at least 50% of ecstasy pills sold in the UK and the rest of Europe may contain mCPP as the primary active ingredient (EMCDDA). Following oral administration of mCPP to healthy human male volunteers, the elimination half-life ranges from 2.6 to 6.1 hours with a wide variation in peak blood levels and bioavailability (EMCDDA). The negative effects of mCPP, often typical of a serotonin syndrome, include anxiety, dizziness, confusion, shivering, sensitivity to light and noise, fear of losing control, migraine and panic attacks (EMCDDA).

Another piperazine derivative commonly found in party pills is TFMPP. TFMPP acts as a non-selective serotonin receptor agonist, in addition to boosting synaptic serotonin levels by blocking serotonin reuptake and increasing its release (Nikolova & Danchev, 2008). It has no therapeutic use, but has been sold as a recreational drug used as a 'legal' alternative to illicit drugs such as Lysergic acid diethylamide (LSD) and MDMA. TFMPP has properties similar to the stimulant effects of ecstasy, but taken in larger doses it promotes hallucinogenic reactions (Nikolova & Danchev, 2008). It is nearly always found in combination with BZP, with which it has a synergistic relationship. The BZP/TFMPP combination leads to increases in dopamine and serotonin levels greater than those observed when either is taken individually (Baumann et al., 2005). This allows manufacturers to lower the dose of each without compromising the effect of the drugs. TFMPP has been shown to be extensively metabolised (Staack et al., 2003), mainly by hydroxylation of the aromatic ring and by degradation of the piperazine moiety to N-(3-trifluoromethylphenyl)ethylenediamine, N-(hydroxyl-trifluoromethylphenyl)ethylenediamine, 3-trifluoromethylaniline, and hydroxyl-3-trifluoromethylaniline, while phase II reactions included glucuronidation, sulphation and acetylation of phase I metabolites.

MeOPP (synonyms: 1-(4-methoxyphenyl)piperazine, Paraperazine, 4-MeOPP) is another piperazine derivative which has been sold as an ingredient in 'Party Pills', initially in New Zealand and subsequently in other countries around the world (Maurer et al., 2004). It has similar effects to those of ecstasy although much less potent (Nikolova & Danchev, 2008). Like TFMPP it is commonly found in combination with BZP to enhance its effects. Indeed various mixtures of piperazine derivatives have been observed with most consisting of variations of BZP, TFMPP, mCPP and Dibenzylpiperazine (DBZP), sometimes mixed with other substances such as amphetamine, cocaine, ketamine, MDMA and caffeine (EMCDDA; Drug Enforcement Administration [DEA] report 2009). With the increasing criminalisation of phenylpiperazine derivatives such as those discussed above there is a need for a simple, rapid technique allowing for routine testing of these drugs.

Analytical methods which have been used to detect or determine piperazine derivatives include GC-MS and LC-MS (Staack & Maurer 2003; Antia et al., 2010). Peters et al., (2010) present a review of analytical toxicology of emerging drugs of abuse including piperazines. A disadvantage of mass spectrometry-based methods of detection is that they require expensive equipment and highly trained staff. Immunoassays are known in the art as relatively cost effective, simplistic and rapid alternatives to mass-spectrometry based analysis. A commercially available enzyme immunoassay test, the EMIT II plus Ecstasy Assay (SYVA/Dade Behring), has been shown to have cross-reactivity to TFMPP and mCPP at concentrations between 5,000-10,000 ng/ml (Logan et al., 2010). The manufacturers include no information for cross-reactivity with mCPP or TFMPP in kit inserts and detection levels of this kit are insufficient for testing purposes. International Patent Publication No WO2010142974 discloses antibodies and methods for differentiating between metabolic mCPP as a result of an individual taking antidepressant drugs and mCPP which is taken illicitly. However these antibodies are not cross-reactive to other phenylpiperazine derivatives. Hence there remains no readily-available screening test specific for phenylpiperazine derivatives and thus to solve this problem a cost effective and rapid method is required to detect and determine the range of phenylpiperazine derivatives found in designer drugs.

REFERENCES

Antia, U., Tingle, M. D., Russell, B. R. (2010) *J Forensic Sci*, 55(5):1311-8.
Baumann, M. et al. (2005) *Neuropsychopharmacology*, 30: 550-560.
DEA report—
http://www.justice.gov/dea/programs/forensicsci/microgram/mg0509/mg0509.pdf
EMCDDA—http://www.emcdda.europa.eu/publications/drug-profiles/bzp
Fitzgerald S. P. et al. (2005). *Clin. Chem.*, 51: 1165-1176.
Logan, B. K. et al. (2010) *J Anal Toxicol*, 34:587-589.
Maurer, H. H. et al. (2004) *Ther Drug Monit*, 26(2): 127-131.
Nikolova, I. & Danchev, N. (2008) *Biotechnol & Biotechnol Eq*, 22: 652-655.
Peters, F. T. et al. (2010) *Ther Drug Monit*, 32(5): 532-539.
Staack, R. F. & Maurer, H. H. (2003) *J Anal Toxicol*, 27(8):560-568.
Staack, R. F. et al. (2003) *J Mass Spectrom*, 38(9): 971-981.
WO2010142974—Benchikh, E. et al.

SUMMARY OF INVENTION

The current invention describes novel immunogens which are used in the production of novel antibodies with unique binding properties in that they cross-react with a variety of phenylpiperazine derivatives. These antibodies enable methods and kits to detect and/or determine phenylpiperazine derivatives (for example mCPP, TFMPP and MeOPP) in an in vitro sample which are advantageous over currently available analytical methods in terms of cost, ease of use, speed and sensitivity.

DETAILED DESCRIPTION

Unless otherwise stated technical terms as used herein are used according to the conventional usage as known to those skilled in the art.

A first aspect of the current invention relates to a hapten of the general structure:

wherein one of X and Y is H and the other is $-(A)_m$-B-D, A being attached to the aromatic ring, and wherein; A is —C(O)—, O or NH and m=0 or 1; B is a $C_1$-$C_{10}$, preferably a $C_1$-$C_6$, substituted or unsubstituted straight or branched chain alkylene moiety, or arylene moiety, and D is selected from a carboxy, a dithiopyridyl, a maleimide, a hydroxyl, a thiol or an aldehyde moiety.

Optionally, A is attached to the aromatic ring. Further optionally, A is attached to position 3 of the aromatic ring. Still further optionally, A is attached to the meta-position of the aromatic ring. Alternatively, A is attached to position 4 of the aromatic ring. Still further optionally, A is attached to the para-position of the aromatic ring.

Optionally, A is selected from —C(O)—, O, and NH.
Optionally, m=0 or 1.
Optionally, B is a $C_1$-$C_{10}$, preferably a $C_1$-$C_6$, substituted or unsubstituted straight or branched chain alkylene moiety. Further optionally, B is a $C_1$-$C_{10}$, preferably a $C_1$-$C_6$, substituted or unsubstituted straight or branched chain arylene moiety.

Optionally, D is selected from a carboxyl, a dithiopyridyl, a maleimidyl, a hydroxyl, a thiol, and an aldehyde moiety.

Optionally, X is H and Y is $-(A)_m$-B-D, wherein A is attached to position 4 of aromatic ring; wherein A is selected from —C(O)—, O, and NH; wherein m=0 or 1; wherein B is a $C_1$-$C_{10}$, preferably a $C_1$-$C_6$, substituted or unsubstituted straight or branched chain alkylene moiety or arylene moiety; and wherein D is selected from a carboxyl, a dithiopyridyl, a maleimidyl, a hydroxyl, a thiol, and an aldehyde moiety.

Optionally, Y is H and X is $-(A)_m$-B-D, wherein A is attached to position 3 of the aromatic ring; wherein A is selected from —C(O)—, O, and NH; wherein m=0 or 1; wherein B is a $C_1$-$C_{10}$, preferably a $C_1$-$C_6$, substituted or unsubstituted straight or branched chain alkylene moiety or arylene moiety; and wherein D is selected from a carboxyl, a dithiopyridyl, a maleimidyl, a hydroxyl, a thiol, and an aldehyde moiety.

Optionally, one of X and Y is H and the other is $-(A)_m$-$(B)_n$-D; wherein A is attached to the aromatic ring; wherein A is selected from —C(O)—, O, and NH; wherein m=0 or 1; wherein B is a $C_1$-$C_{10}$, preferably a $C_1$-$C_6$, substituted or unsubstituted straight or branched chain alkylene moiety or arylene moiety; wherein n=0 or 1; and wherein D is selected from a carboxyl, a dithiopyridyl, a maleimidyl, a hydroxyl, a thiol, and an aldehyde moiety.

Optionally, Y is H; X is $-(A)_m$-$(B)_n$-D; wherein m=0; wherein n=0; and wherein D is selected from a carboxyl, a dithiopyridyl, a maleimidyl, a hydroxyl, a thiol, and an aldehyde moiety. Further optionally, Y is H; X is $-(A)_m$-$(B)_n$-D; wherein m=0; wherein n=0; and wherein D is carboxyl moiety.

Optionally, X is H; Y is $-(A)_m$-$(B)_n$-D; wherein A is attached to position 4 of the aromatic ring; wherein A is 0; wherein m=1; wherein B is a $C_1$-$C_6$ substituted or unsubstituted straight or branched chain alkylene moiety; wherein n=1; and wherein D is selected from a carboxyl, a dithiopyridyl, a maleimidyl, a hydroxyl, a thiol, and an aldehyde moiety. Further optionally, X is H; Y is $-(A)_m$-$(B)_n$-D; wherein A is attached to position 4 of the aromatic ring; wherein A is 0; wherein m=1; wherein B is a $C_1$ unsubstituted straight or branched chain alkylene moiety; wherein n=1; and wherein D is a carboxyl moiety.

The term "hapten" as used herein describes a pre-immunogenic molecule that stimulates antibody production only when conjugated to a larger carrier molecule.

A second aspect of the current invention relates to an immunogen comprising of a hapten as described above conjugated to an antigenicity-conferring carrier material (accm). The accm can be coupled to the aromatic ring. Optionally, the accm is coupled to position 3 of the aromatic ring. Further optionally, the accm is coupled to the meta-position of the aromatic ring. Alternatively, the accm is coupled to position 4 of the aromatic ring. Still further optionally, the accm is coupled to the para-position of the aromatic ring. In the preferred embodiment of the current invention the accm is coupled to D, when X or Y is -(A)$_m$-B-D. It is understood that the accm forms a bond, optionally a covalent bond, with D. The term "immunogen" as used herein, describes an entity that induces an immune response such as production of antibodies or a T-cell response in a host animal. The accm can be any material that makes all or part of the hapten susceptible to antibody recognition and binding. For example the accm can be a protein, a protein fragment, a synthetic polypeptide or a semi-synthetic polypeptide. Illustrative examples of useful antigenicity-conferring carrier materials are bovine serum albumin (BSA), egg ovalbumin, bovine gamma globulin, bovine thyroglobulin (BTG), keyhole limpet haemocyanin (KLH) etc. Preferably the accm is BTG.

Optionally, the immunogen comprises:
(a) a hapten having the general structure described above; wherein Y is H; X is -(A)$_m$-(B)$_n$-D; wherein m=0; wherein n=0; wherein D is carboxyl moiety; and
(b) an accm selected from bovine serum albumin (BSA), egg ovalbumin, bovine gamma globulin, bovine thyroglobulin (BTG), and keyhole limpet haemocyanin (KLH).

Optionally, the immunogen comprises:
(a) a hapten having the general structure described above; wherein X is H; Y is -(A)$_m$-(B)$_n$-D; wherein A is attached to position 4 of the aromatic ring; wherein A is O; wherein m=1; wherein B is a C$_1$ unsubstituted straight chain alkylene moiety; wherein n=1; wherein D is a carboxyl moiety; and
(b) an accm selected from bovine serum albumin (BSA), egg ovalbumin, bovine gamma globulin, bovine thyroglobulin (BTG), and keyhole limpet haemocyanin (KLH).

Figure 2:
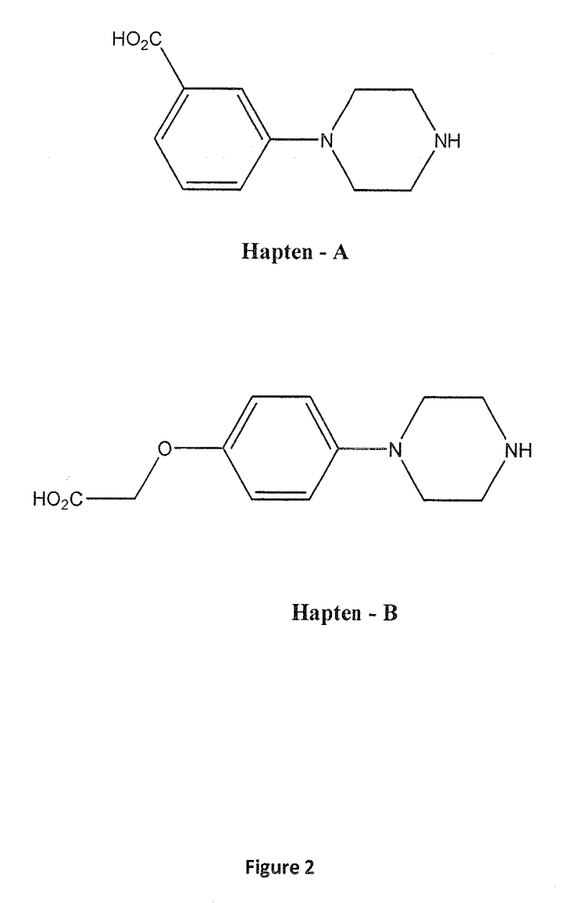

A preferred embodiment of the current invention is an immunogen as discussed supra which is either 1-(3-carboxyphenyl)piperazine (Hapten-A, FIG. 2) or 1-(4-carboxymethyletherphenyl)piperazine (Hapten-B, FIG. 2) coupled to an antigenicity-conferring carrier material. Examples of suitable carrier materials are BTG, BSA or KLH.

The immunogens obtained in the current invention are then administered to mammalian hosts to elicit production of specific antibodies, optionally polyclonal antibodies, which are then used to develop immunoassays for phenylpiperazine derivatives, employing labelled conjugates as detection reagents.

Another aspect of the current invention is an antibody raised against an immunogen as described above. A preferred antibody of the current invention is an antibody raised against an immunogen as described above comprising a hapten in which Y=H and X=-(A)$_m$-(B)$_n$-D; A being attached to the aromatic ring, and wherein A is —C(O)—, O or NH and m=0 or 1; B is a C$_1$-C$_{10}$, preferably a C$_1$-C$_6$, substituted or unsubstituted straight chain alkylene moiety, or arylene moiety; n=0 or 1; D is selected from a carboxy, a dithiopyridyl, a maleimide, a hydroxyl, a thiol or an aldehyde moiety, and the hapten is conjugated to an antigenicity-conferring carrier material. An even more preferred antibody of the current invention is an antibody raised against 1-(3-carboxyphenyl)piperazine (Hapten A, FIG. 2) coupled to an antigenicity-conferring carrier material and having specificity for 1-(3-methylphenyl)piperazine with an IC$_{50}$ value of less than 50 ng/ml, preferably less than 10 ng/ml, most preferably around 1 ng/ml, which is optionally further characterised by having cross-reactivity to at least one of 1-(3-chlorophenyl)piperazine, 1-phenylpiperazine, 1-(4-methoxyphenyl)piperazine, 1-(4-hydroxyphenyl)piperazine, 1-(4-fluorophenyl)piperazine, 1-(3-hydroxyphenyl)piperazine and 1-(3-trifluoromethylphenyl)piperazine.

An additional preferred antibody of the current invention is an antibody raised against an immunogen as described above comprising a hapten in which X=H and Y=-(A)$_m$-B-D, A being attached to the aromatic ring and wherein A is —C(O)—, O or NH and m=0 or 1; B is a C$_1$-C$_{10}$, preferably a C$_1$-C$_6$, substituted or unsubstituted straight chain alkylene moiety, or arylene moiety; D is selected from a carboxy, a dithiopyridyl, a maleimide, a hydroxyl, a thiol or an aldehyde moiety, and the hapten is conjugated to an antigenicity-conferring carrier material. An even more preferred antibody is one raised against an immunogen which is 1-(4-carboxymethyletherphenyl)piperazine (Hapten B, FIG. 2) coupled to an antigenicity-conferring carrier material and having specificity for 1-(3-methylphenyl)piperazine with an IC$_{50}$ value of around less than 50 ng/ml, preferably less than 10 ng/ml, most preferably around 1 ng/ml, which is optionally further characterised by having cross-reactivity to at least one of 1-(3-chlorophenyl)piperazine, 1-phenylpiperazine, 1-(4-methoxyphenyl)piperazine, 1-(4-hydroxyphenyl)piperazine, 1-(4-fluorophenyl)piperazine, 1-(3-hydroxyphenyl)piperazine, (3-trifluoromethylphenyl)piperazine and 1-(2-methoxyphenyl)piperazine.

The term "antibody" as used herein refers to an immunoglobulin or immunoglobulin-like molecule. In a preferred embodiment of the current invention the antibodies are monoclonal antibodies but the skilled person will understand that any type of immunoglobulin molecule or fragment thereof can be used, for example polyclonal antibodies, Fab fragments, scFv fragments and any other antigen binding fragments all of which fall within the scope of the current invention. Monoclonal antibodies may be produced by methods known to those skilled in the art (as described in 'Monoclonal antibody production techniques and application' by L. B Schook, 1987, Dekker, ISBN 0824776402). Any suitable host animal may be used, preferably a mammalian animal for example, but not limited to sheep, rabbit, mouse, guinea pig or horse.

When used in reference to an antibody, the word 'specific' or 'specificity' in the context of the current invention refers to the analyte that is preferably bound by the antibody, as gauged by a suitable metric such as the cross-reactivity. As is known by one skilled in the art, for cross-reactivity to be of practical use the analyte-specific antibody must display a high sensitivity as measured by a suitable metric such as the IC$_{50}$. The IC$_{50}$ is a common measure of antibody sensitivity for immunoassays. For the current invention, a high sensitivity is an IC$_{50}$ of less than 50 ng/ml, preferably less than 10 ng/ml, most preferably around 1 ng/ml. In the current invention an IC$_{50}$ of 'around 1 ng/ml' refers to antibodies with IC$_{50}$ values from about 0.5 ng/ml to about 1.5 ng/ml. It is recognized by those skilled in the art that for immunoassays which utilize a competitive format, the exact IC$_{50}$ value varies slightly depending on the nature of the detecting agent used to compete with the analyte in the sample.

The antibodies of the invention may be used in isolation or in combinations in a method to detect or determine one or more phenylpiperazine derivatives in a sample (examples are shown in FIG. 1). Most preferably the antibodies of the invention are used in a method to detect or determine one or more of 1-phenylpiperazine, 1-(4-hydroxyphenyl)piperazine, 1-(3-chlorophenyl)piperazine, 1-(4-methoxyphenyl)

piperazine, 1-(3-methylphenyl)piperazine, 1-(3-trifluoromethylphenyl)piperazine, 1-(4-chlorophenyl)piperazine, 1-(4-fluorophenyl)piperazine and 1-(2-methoxyphenyl) piperazine in an in vitro sample, the method comprising contacting the sample with the antibody or antibody combination and optionally one or more detecting agents, deducing the presence of or amount of one or more of 1-phenylpiperazine, 1-(4-hydroxyphenyl)piperazine, 1-(3-chlorophenyl)piperazine, 1-(4-methoxyphenyl)piperazine, 1-(3-methylphenyl)piperazine, 1-(3-trifluoromethylphenyl) piperazine, 1-(4-chlorophenyl)piperazine, 1-(4-fluorophenyl)piperazine and 1-(2-methoxyphenyl)piperazine; optionally by measuring the detecting agent(s) and deducing from a calibrator the presence of or amount of one or more of 1-phenylpiperazine, 1-(4-hydroxyphenyl)piperazine, 1-(3-chlorophenyl)piperazine, 1-(4-methoxyphenyl)piperazine, 1-(3-methylphenyl)piperazine, 1-(3-trifluoromethylphenyl) piperazine, 1-(4-chlorophenyl)piperazine, 1-(4-fluorophenyl)piperazine and 1-(2-methoxyphenyl)piperazine. In a preferred embodiment the combination is one antibody raised against an immunogen consisting of 1-(3-carboxyphenyl)piperazine (Hapten A, FIG. 2) coupled to an antigenicity-conferring carrier material and one antibody raised against an immunogen consisting of 1-(4-carboxymethyletherphenyl)piperazine (Hapten B, FIG. 2) coupled to an antigenicity-conferring carrier material. The preferred accm is BTG. Unexpectedly this combination of two antibodies derived from immunogens conjugated through two adjacent positions on the haptens and a single conjugate or labelled detecting agent, produced a sensitive assay capable of detecting or determining a wide range of piperazine derivatives (Table 1).

Another preferred embodiment of the invention is a method to detect or determine one or more phenylpiperazine derivative(s) in an in vitro sample, the method comprising contacting the sample with an antibody raised against an immunogen consisting of 1-(3-carboxyphenyl)piperazine (Hapten A, FIG. 2) coupled to an antigenicity-conferring carrier material and optionally one or more detecting agents deducing the presence of or amount of one or more phenylpiperazine derivative(s), optionally by measuring the detecting agent(s) and deducing from a calibrator the presence of or amount of one or more phenylpiperazine derivative(s).

A further embodiment of the invention is a method to detect or determine one or more phenylpiperazine derivative(s) in an in vitro sample, the method comprising contacting the sample with an antibody raised against an immunogen consisting of 1-(4-carboxymethyletherphenyl) piperazine (Hapten B, FIG. 2) coupled to an antigenicity-conferring carrier material and one or more detecting agents, measuring the detecting agent(s) and deducing from a calibrator, the presence of or amount of one or more phenylpiperazine derivative(s).

The terms "detect" or "detecting" as used herein refers to qualitatively analysing for the presence or absence of a substance, while "determining" refers to quantitatively analysing for the amount of a substance present. As the antibodies of the current invention are able to bind to several molecules quantitative analysis will take the form of measuring the calibrator-equivalent value. The person skilled in the art will also recognise that for the purposes of a positive assay a suitable cut-off value could be implemented. The sample in the current invention can be any biological sample from which a phenylpiperazine derivative can be detected. Preferably the sample is taken from the group of whole blood, plasma, serum, and urine, however any suitable biological sample from which a phenylpiperazine could be detected may be used, for example hair or oral fluid.

The detecting agents of the current invention comprise of a hapten, preferably one as described herein, conjugated to a detectable labelling agent. Preferably the labelling agent is selected from an enzyme, a luminescent substance, a radioactive substance or a mixture thereof. More preferably the labelling agent is an enzyme, preferably a peroxidase and most preferably horseradish peroxidase. Most preferably the detecting agent is 1-(4-carboxymethyletherphenyl)piperazine covalently bonded to a detectable labelling agent. An example of a suitable labelling agent is horseradish peroxidise.

The invention also describes kits for detecting or determining one or more phenylpiperazine derivatives. Preferably the kit is one in which the one or more piperazine derivatives detected or determined are 1-phenylpiperazine, 1-(4-hydroxyphenyl)piperazine, 1-(3-chlorophenyl)piperazine, 1-(4-methoxyphenyl)piperazine, 1-(3-methylphenyl) piperazine, 1-(3-trifluoromethylphenyl)piperazine, 1-(4-chlorophenyl)piperazine, 1-(4-fluorophenyl)piperazine and 1-(2-methoxyphenyl)piperazine. In a preferred embodiment of the current invention the kit comprises one or more of the antibodies derived from the immunogens described above and at least one detecting agent.

In a further preferred embodiment the kit comprises one antibody derived from hapten A (FIG. 2) and one antibody derived from hapten B (FIG. 2) along with at least one detecting agent, and the one or more piperazine derivatives detected or determined are 1-phenylpiperazine, 1-(4-hydroxyphenyl)piperazine, 1-(3-chlorophenyl)piperazine, 1-(4-methoxyphenyl)piperazine, 1-(3-methylphenyl)piperazine, 1-(3-trifluoromethylphenyl)piperazine, 1-(4-chlorophenyl)piperazine, 1-(4-fluorophenyl)piperazine and 1-(2-methoxyphenyl)piperazine. The antibodies of the kits are preferably tethered to a suitable solid support such as a chip. Although the solid support can be of any suitable shape such as a bead or a slide and of any suitable material such as silicon, glass or plastic, the solid support is preferably a ceramic chip. The kit may further include calibrators and one or more detecting agents and optionally includes instructions for the use of the antibodies of the kit and if incorporated, the calibrators and detecting agents, for detecting and determining phenylpiperazine derivatives.

General Methods, Examples and Results

Immunoassay Development

The process of developing an immunoassay is well known to the person skilled in the art (as described in 'Immunoassay: A practical guide' by Brian Law, Taylor and francis Ltd, ISBN 0-203-48349-9). Briefly, for a competitive immunoassay in which the target analyte is a non-immunogenic molecule such as a hapten, the following process is conducted: antibodies are produced by immunizing an animal, preferably a mammalian animal, by repeated administration of an immunogen. The serum from the immunized animal is collected when the antibody titre is sufficiently high. A detecting agent is added to a sample containing the target analyte and the raised antibodies, and the detecting agent and analyte compete for binding to the antibodies. The process may comprise fixing said serum antibodies to a backing substrate such as a polystyrene solid support or a ceramic chip. The antibodies can be polyclonal or monoclonal using standard techniques. The signal emitted in the immunoassay is proportionate to the amount of detecting agent bound to the antibodies which in turn is inversely proportionate to the analyte concentration. The signal can be detected or quantified by comparison with a calibrator.

Preparation of Haptens, Immunogens and Detecting Agents

Although haptens provide defined structural epitopes, they are not in themselves immunogenic and therefore need to be conjugated to carrier materials, which will elicit an immunogenic response when administered to a host animal. Appropriate carrier materials commonly contain poly(amino acid) segments and include polypeptides, proteins and protein fragments. Illustrative examples of useful carrier materials are bovine serum albumin (BSA), egg ovalbumin, bovine gamma globulin, bovine thyroglobulin (BTG), keyhole limpet haemocyanin (KLH) etc. Alternatively, synthetic poly(amino acids) having a sufficient number of available amino groups, such as lysine, may be employed [examples of synthetic poly(amino acids)?], as may any other synthetic or natural polymeric materials bearing reactive functional groups [examples of synthetic or natural polymeric materials?]. Carbohydrates, yeasts or polysaccharides may also be conjugated to the hapten to produce an immunogen. The haptens can also be coupled to a detectable labelling agent such as an enzyme (for example, horseradish peroxidase), a substance having fluorescent properties or a radioactive label for the preparation of detecting agents (conjugates) for use in the immunoassays. The fluorescent substance may be, for example, a monovalent residue of fluorescein or a derivative thereof. Immunogen formation for the invention described herein involves conventional conjugation chemistry as described in "Bioconjugation Techniques" by Greg T. Hermanson, Academic Press, pages 419-455 and "Bioconjugation" by Mohammed Aslam and Alastair Dent, ISBN 1-56159-161-0 (1998) pages 364-482. In order to confirm that adequate conjugation of the hapten to carrier material has been achieved, prior to immunisation, each immunogen is evaluated using matrix-assisted UV laser desorption/ionisation time-of-flight mass spectroscopy (MALDI-TOF MS). In the case of the preferred carrier materials, BSA, BTG and KLH, a minimum of 6 molecules of hapten per molecule of carrier material is preferred.

General Procedure for MALDI-TOF Analysis of Immunogens.

MALDI-TOF mass spectrometry was performed using a Voyager STR Biospectrometry Research Station laser-desorption mass spectrometer coupled with delayed extraction. An aliquot of each sample to be analysed was diluted in 0.1% aqueous trifluoroacetic acid (TFA) (Sigma) to create 1 mg/ml sample solutions. Aliquots (1 µl) were analysed using a matrix of sinapinic acid (Sigma) and bovine serum albumin (Fluka) was used as an external calibrant.

Preparation of Antisera

In order to generate polyclonal antisera, 2 mg of an immunogen of the present invention is prepared in PBS, mixed at a ratio of 50% Immunogen in PBS with 50% Freund's Complete adjuvant (Sigma, Product Number—F5881) and emulsified by repeatedly passing the mixture through a tip on the end of a 1 ml syringe, until it reaches the required semi-solid consistency. 1 ml of the mixture is then injected into a host animal, such as rabbit, sheep, mouse, guinea pig or horse. Sheep are the preferred host animal. Further injections (boosts) are administered on a monthly basis (1 mg of immunogen is prepared in PBS and mixed at a ratio of 50% Immunogen in PBS with 50% of Freunds Incomplete Adjuvent, Sigma product Number—F5506) until the required titre is achieved. Serum is sampled for evaluation of the antibody titre.

Briefly, blood is collected by applying pressure to the exposed jugular vein and inserting a clean 14 gauge hypodermic needle to remove 500 ml of blood per sheep, under gravity. The blood is stored at 37° C. for a minimum of 1 hour before the clots are separated from the side of the centrifuge bottles using disposable 1 ml pipettes (ringing). The samples are stored at 4° C. overnight.

Samples are then centrifuged at 4200 rpm for 30 minutes at 4° C. The serum is poured off and centrifuged again, at 10,000 rpm for 15 minutes at 4° C., before being aliquoted and stored at <−20° C.

The Immunoglobulin (Ig) fraction is extracted from the antisera via caprylic acid/ammonium sulphate precipitation of immunoglobulin.

The antibody titre is evaluated by coating a microtitre plate (Thermo Fisher Scientific NUNC, 468667) with antibody (125 µl/well) in coating buffer (10 mM Tris pH 8.5) at 37° C. for 2 hours. The plate is then washed 4 times over 10 minutes with working strength TBST. 50 µl of sample/standard (1-phenylpiperazine) is added to the appropriate wells in triplicate, followed by 75 µl of hapten-HRP conjugate and incubated at 25° C. for 1 hour. The plate is then washed and 125 µl of TMB (Randox, 4380-15) added to each well and left at room temperature for 20 mins in the dark. The reaction is stopped using 125 µl of 0.2M sulphuric acid. The absorbances are read at 450 nm with an ELISA microplate reader (BIO-TEK Instruments, E1x800) and the means calculated. Antibody sensitivity can then be determined.

When the optimal titre has been attained, the host animal is bled to yield a suitable volume of specific antiserum (overall this results in 20 bleeds in total, with approximately 200 ml of antiserum achieved per bleed). The degree of antibody purification required depends on the intended application. For many purposes, there is no requirement for purification, however, in other cases, such as where the antibody is to be immobilised on a solid support, purification steps can be taken to remove undesired material and eliminate non-specific binding.

Various purification steps are available if required, including Immunoglobulin Precipitation (as described above), Antigen-specific affinity purification, Size-exclusion chromatography and Ion Exchange Chromatography.

Figure 3:
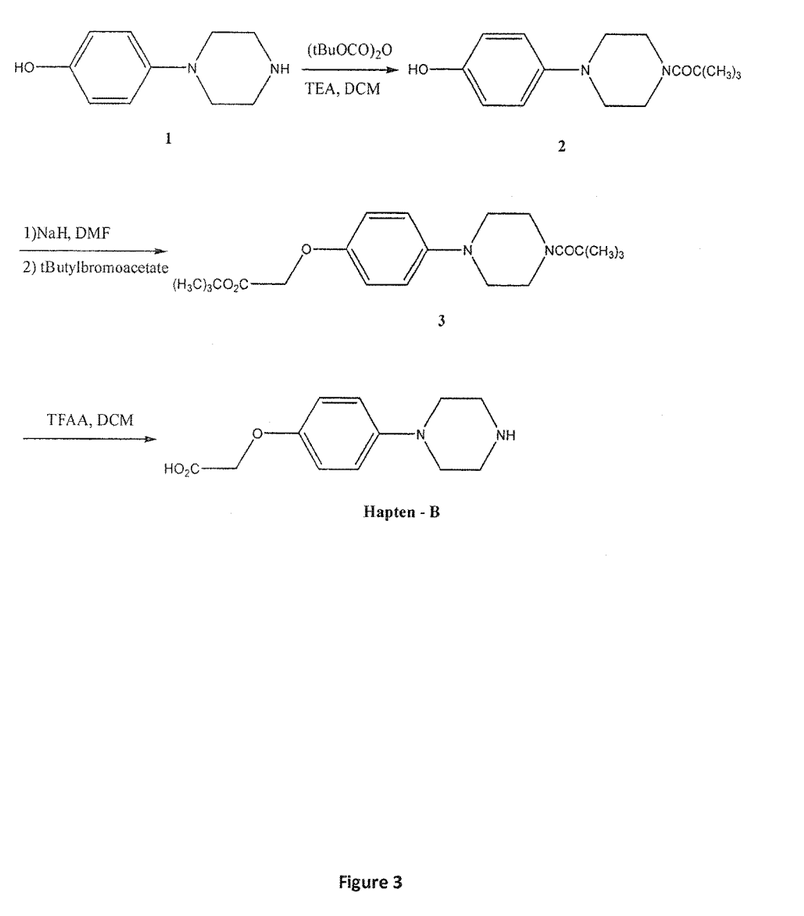

EXAMPLES (Numbers in Bold Refer to Structures in FIG. 3)

Example 1

Conjugation of 3-(carboxyphenyl)piperazine (Hapten-A) to BSA (to Form Immunogen-I)

To a solution of 3-(carboxyphenyl)piperazine (Hapten-A) (30.9 mg, 0.15 mM) in DMF (1.0 ml) was added N,N-dicyclohexylcarbodiimide (DCC) (33.08 mg, 0.16 mM) and N-hydroxysuccinimide (18.7 mg, 0.16 mM) and the mixture was stirred at room temperature overnight. The dicyclohexylurea formed was removed by filtration and the solution was added dropwise to a solution of BSA (150 mg, 2.3 µmol) in 50 mM sodium bicarbonate solution (pH 8.5) (10 ml). The mixture was then stirred overnight at 4° C. The solution was then dialysed against 50 mM phosphate buffer pH 7.2 (3 changes) for 24 hours at 4° C., and freeze-dried to give Immunogen-I.

MALDI results showed 14.07 molecules of Hapten-A had been conjugated to one molecule of BSA.

Example 2

Conjugation of 3-(carboxyphenyl)piperazine (Hapten-A) to BTG (to Form Immunogen-II)

To a solution of 3-(carboxyphenyl)piperazine (Hapten-A) (41.8 mg, 0.203 mmol) in DMF (1.0 ml) was added N,N-dicyclohexylcarbodiimide (DCC) (46.01 mg, 0.223 mmol) and N-hydroxysuccinimide (25.66 mg, 0.223 mmol) and the mixture was stirred at room temperature overnight. The dicyclohexylurea formed was removed by filtration and the solution was added dropwise to a solution of BTG (150 mg, 2.25 μmol) in 50 mM sodium bicarbonate solution (pH 8.5) (10 ml). The mixture was then stirred overnight at 4° C. The solution was then dialysed against 50 mM phosphate buffer pH 7.2 (3 changes) for 24 hours at 4° C., and freeze-dried to give Immunogen-II.

Example 3

Conjugation of 3-(carboxyphenyl)piperazine (Hapten-A) to HRP

EDC hydrochloride (10 mg) was dissolved in water (0.5 ml) and immediately added to a solution of 3-(carboxyphenyl)piperazine (Hapten-A) (2 mg) in DMF (0.2 ml). After mixing, this solution was added dropwise to a solution of HRP (20 mg) in water (1 ml). Sulfo-NHS (5 mg) was added and the reaction mixture was incubated in the dark at room temperature overnight. Excess hapten was removed with double PD-10 columns (Pharmacia) in series, pre-equilibrated with PBS at pH 7.2. The hapten-A-HRP conjugate was then dialysed overnight against 10 L of PBS at pH 7.2 at 4° C.

Example 4

Preparation of 4-BOC-1-(4-hydroxyphenyl)piperazine 2

To a suspension of 1-(4-hydroxyphenyl)piperazine 1 (8.91 g, 0.05 mol) in dichloromethane (200 ml) was added TEA (10.5 ml, 0.075 mol) and BOC anhydride (9.8 g, 0.052 mol) and the mixture was stirred at room temperature overnight. The solution was then washed by water (1×100 ml), brine (1×100 ml), dried over sodium sulphate, filtered and concentrated to dryness. The crude product obtained was purified by flash chromatography on silica gel using ethyl acetate/hexane (50/50) to give the 4-boc-1-(4-hydroxyphenyl)piperazine 2 (10.1 g, 77%).

Example—5

Preparation of the Ester 3

To a suspension of sodium hydride (NaH) (1.53 g, 0.046 mol) in DMF (50 ml) under nitrogen was added dropwise a solution of N-boc-4-hydoxybenzylpiperazine 3 (8.0 g, 0.038 mol) in DMF (50 ml) and the mixture was stirred and heated at 60° C. for 1 hour. The mixture was then cooled to room temperature and to it was added dropwise a solution of terbutyl bromoacetate (11.1g, 0.057) in DMF (25 ml) and the mixture was stirred and heated at 60° C. for 4 hours. The solution was then cooled to RT and the DMF was removed under vacuum. Ethyl acetate (250 ml) was added to the crude product and then washed by water (100 ml) and brine (100 ml). The solution was then dried over sodium sulphate filtered and concentrated to dryness. The crude product obtained was purified by chromatography on silica gel using ethyl acetate/hexane (1/1) to give the ester 3 (9.6 g, 67.1%) as a clear oil.

Example—6

Preparation of the 1-(4-carboxymethyletherphenyl)piperazine TFA Salt (Hapten-B)

To a solution of the ester 3 (3.5 g, 0.009 mol) in dichloromethane (100 ml) was added trifluoroacetic acid (TFA) (30 ml) and the solution was stirred at room temperature overnight. The solution was concentrated to dryness and the crude product obtained was triturated with ether to give a white solid of the Hapten-B as TFA salt (2.3 g, 73%) as TFA salt (FIG. 3).

Example 7

Conjugation of 1-(4-carboxymethyletherphenyl)piperazine TFA Salt (Hapten-B) to BSA (to Form Immunogen-III)

To a solution of 1-(4-carboxymethyletherphenyl)piperazine TFA salt (Hapten-B) (52.5 mg, 0.15 mM) in DMF (1.0 ml) was added N,N-dicyclohexylcarbodiimide (DCC) (33.08 mg, 0.16 mM) and N-hydroxysuccinimide (18.7 mg, 0.16 mM) and the mixture was stirred at room temperature overnight. The dicyclohexylurea formed was removed by filtration and the solution was added dropwise to a solution of BSA (150 mg, 2.3 μmol) in 50 mM sodium bicarbonate solution (pH 8.5) (10 ml). The mixture was then stirred overnight at 4° C. The solution was then dialysed against 50 mM phosphate buffer pH 7.2 (3 changes) for 24 hours at 4° C., and freeze-dried to give Immunogen-III.

MALDI results showed 6.03 molecules of Hapten-B had been conjugated to one molecule of BSA.

Example 8

Conjugation of 1-(4-carboxymethyletherphenyl)piperazine TFA Salt (Hapten-B) to BTG (to Form Immunogen-IV)

To a solution of 1-(4-Carboxymethyletherphenyl)piperazine TFA salt (Hapten-B) (71.1 mg, 0.203 mmol) in DMF (1.0 ml) was added N,N-dicyclohexylcarbodiimide (DCC) (46.01 mg, 0.223 mmol) and N-hydroxysuccinimide (25.66 mg, 0.223 mmol) and the mixture was stirred at room temperature overnight. The dicyclohexylurea formed was removed by filtration and the solution was added drop wise to a solution of BTG (150 mg, 2.25 μmol) in 50 mM sodium bicarbonate solution (pH 8.5) (10 ml). The mixture was then stirred overnight at 4° C. The solution was then dialysed against 50 mM phosphate buffer pH 7.2 (3 changes) for 24 hours at 4° C., and freeze-dried to give immunogen-IV.

Example 9

Conjugation of 1-(4-carboxymethyletherphenyl)piperazine TFA Salt (Hapten-B) to HRP EDC hydrochloride (10 mg) was dissolved in water (0.5 ml) and immediately added to a solution of 1-(4-Carboxymethyletherphenyl)piperazine TFA salt (Hapten-B) (2 mg) in DMF (0.2 ml). After mixing, this solution was added dropwise to a solution of HRP (20 mg) in water (1 ml). Sulfo-NHS (5 mg) was added and the reaction mixture was incubated in the dark at room temperature overnight. Excess hapten was removed with double PD-10 columns (Pharmacia) in series, pre-equilibrated with PBS at pH 7.2. The hapten-HRP conjugate was then dialysed overnight against 10 L of PBS at pH 7.2 at 4° C.

Example 10

Immunoassays for Piperazine Derivatives

A semi-automated Evidence Investigator analyser (Randox Laboratories Ltd., Crumlin, UK) was used as the platform for a biochip assay for the detection of phenylpiperazines.

Immunogens were administered to 16-month old Suffolk sheep on a monthly basis to provide target specific polyclonal antisera. The immunisation mixture was prepared by adding 2 mg of immunogen prepared in PBS at a ratio of 50% Immunogen/PBS with 50% Freund's Complete adjuvant (Sigma, Product Number—F5881) and emulsifying the mixture to prepare the final product for immunisation. On day 0, 1 ml of the mixture described above was administered intramuscularly to adult sheep. Subsequent boosts (a total of 20 boosts) were administered intramuscularly to each sheep every 30 days. Freund's complete adjuvant (Sigma, Product Number—F5881) was used for primary immunizations and Freund's incomplete adjuvant (Sigma product Number—F5506) was used for all subsequent injections. Routine bleeds were taken between boosts to monitor the antibody titre and sensitivity, using hapten B conjugated to Horseradish peroxidase in a competitive ELISA, testing cross reactivity to 1-(3-Chlorophenyl)piperazine. In the case of the combination immunoassay, immunogens II and IV were administered to separate sheep and the resulting antisera were combined in a 1:1 ratio to form the antibody blend (1 ml of antisera from the sheep administered with Immunogen II was combined with 1 ml of antisera from the sheep administered with Immunogen IV). IgG was extracted from antisera and purified as described above, and the purified antibodies were immobilised on a biochip (9 mm×9 mm) (Randox Laboratories Ltd). The assay was based on competition for binding sites of a polyclonal antibody between Hapten B-HRP conjugate (Example 9) and phenylpiperazines and potential cross-reactants. The antibodies were immobilised and stabilised onto the biochip surface as previously described (Fitzgerald et al., 2005). Assay diluent (155 μL), calibrator/phenylpiperazine or potential cross-reactant (25 μL) followed by Hapten-B conjugate (120 μL) were added to the appropriate biochip. The biochips were then incubated for 30 minutes at 30° C. on a thermoshaker set at 370 rpm. The biochips were then subjected to 2 quick wash cycles using the wash buffer provided, followed by 4×2 minute wash cycles. 250 μL of signal (1:1 luminol+peroxide, v/v) was then added to each biochip, and after 2 minutes the biochip carrier was imaged in the Evidence Investigator analyser.

Results

Calibration curves were generated using the Biochip-based immunoassay. $IC_{50}$ values were calculated from the graphs by taking 50% of the signal from the zero calibrator and reading the corresponding value on the x-axis, equivalent to the concentration of unlabelled ligand which reduces specific binding of labelled ligand by 50%. Specificity (measured as percentage cross-reactivity–[$IC_{50}$ (analyte)/$IC_{50}$ (cross-reactant)]×100) was also tested against a range of piperazine derivatives and other compounds sharing structural features (see table 1).

TABLE 1

Percentage cross-reactivity for two antibodies of the current invention (antibody 1 raised against Immunogen IV and antibody 2 raised against Immunogen II) standardized to 1-(3-chlorophenyl)piperazine monohydrochloride.

| Analyte | Antibody 1 | | Antibody 2 | | Combination of antibodies 1 & 2 | |
|---|---|---|---|---|---|---|
| | Cross-reactivity (%) | $IC_{50}$ (ng/ml) | Cross-reactivity (%) | $IC_{50}$ (ng/ml) | Cross-reactivity (%) | $IC_{50}$ (ng/ml) |
| 1-(3-Chlorophenyl)piperazine (mCPP) | 100 | 0.907 | 100 | 2.554 | 100 | 2.075 |
| 1-(3-Methylphenyl)piperazine (mMPP) | 129 | 0.840 | 230 | 1.697 | 191 | 1.418 |
| 1-phenylpiperazine | 106 | 1.017 | 140 | 2.795 | 125 | 2.163 |
| 1-(4-Methoxyphenyl)piperazine (pMeOPP) | 68 | 0.868 | 20 | 19.771 | 26 | 10.226 |
| 1-(4-hydroxyphenyl)piperazine | 57 | 1.029 | 10 | 28.195 | 18 | 15.032 |
| 1-(4-Fluorophenyl)piperazine | 54 | 1.085 | 38 | 7.646 | 51 | 5.113 |
| 1-(3-hydroxyphenyl)piperazine | 31 | 3.469 | 156 | 2.504 | 95 | 2.848 |
| 1-(3-Trifluoromethylphenyl)piperazine (mTFMPP) | 13 | 7.620 | 61 | 4.831 | 44 | 5.958 |
| 4-(4-Chlorophenyl)-4-Hydroxypiperidine | <1 | 218.980 | <1 | NA | <1 | NA |
| 1-benzylpiperazine (BZP) | <1 | 232.706 | <1 | NA | <1 | NA |
| 1-(2- | <1 | 335.160 | 34 | 8.770 | 17 | 15.553 |

TABLE 1-continued

Percentage cross-reactivity for two antibodies of the current invention (antibody 1 raised against Immunogen IV and antibody 2 raised against Immunogen II) standardized to 1-(3-chlorophenyl)piperazine monohydrochloride.

| Analyte | Antibody 1 | | Antibody 2 | | Combination of antibodies 1 & 2 | |
|---|---|---|---|---|---|---|
| | Cross-reactivity (%) | IC$_{50}$ (ng/ml) | Cross-reactivity (%) | IC$_{50}$ (ng/ml) | Cross-reactivity (%) | IC$_{50}$ (ng/ml) |
| Methoxyphenyl)piperazine | | | | | | |
| Mephedrone | <1 | NA | <1 | NA | <1 | NA |
| Mescaline | <1 | NA | <1 | NA | <1 | NA |
| (+)-Pseudoephedrine | <1 | NA | <1 | NA | <1 | NA |
| MDPBP | <1 | NA | <1 | NA | <1 | NA |
| JWH-018 | <1 | NA | <1 | NA | <1 | NA |
| JWH-250 | <1 | NA | <1 | NA | <1 | NA |
| Salvinorin A | <1 | NA | <1 | NA | <1 | NA |
| Piperazine | <1 | NA | <1 | NA | <1 | NA |
| 1-Methyl-3-phenylpiperazine | <1 | NA | <1 | NA | <1 | NA |
| Trazadone | <1 | NA | <1 | NA | <1 | NA |
| MCPCP | <1 | NA | <1 | NA | <1 | NA |
| 3-Amino-2-hydroxybenzotrifluoride | <1 | NA | <1 | NA | <1 | NA |

We claim:

1. A polyclonal antibody raised against an immunogen, wherein the immunogen is a conjugate of 1-(4-carboxymethyletherphenyl)piperazine linked through the carboxy group to bovine thyroglobulin;
   wherein the polyclonal antibody has a cross-reactivity of 100% to 1-(3-chlorophenyl)piperazine, 129% to 1-(3-methylphenyl)piperazine), 106% to 1-phenylpiperazine, 68% to 1-(4-methoxyphenyl)piperazine, 57% to 1-(4-hydroxyphenyl)piperazine, 54% to 1-(4-fluorophenyl) piperazine, 31% to 1-(3-hydroxypheyl)piperazine, 13% to 1-(3-trifluoromethylphenyl)piperazine, and less than 1% to each of 4-(4-chlorophenyl)-4-hydroxypiperidine, 1-benzylpiperazine, 1-(2-methoxyphenyl)piperazine, mephedrone, mescaline, (+)-pseudoephedrine, MDPBP, JWH-018, JWH-250, salvinorin A, piperazine, 1-methyl-3-phenylpiperazine, trazodone, MCPCP and 3-amino-2-hydroxybenzotrifluoride;
   wherein the cross reactivity is measured in the presence of a detecting agent, wherein the detecting agent is a conjugate of 1-(4-carboxymethyletherphenyl)piperazine linked through the carboxy group to horseradish peroxidase.

2. A polyclonal antibody raised against an immunogen, wherein the immunogen is a conjugate of 1-(3-carboxyphenyl)piperazine linked through the carboxy group to bovine thyroglobulin;
   wherein the polyclonal antibody has a cross-reactivity of 100% to 1-(3-chlorophenyl)piperazine, 230% to 1-(3-methylphenyl)piperazine), 140% to 1-phenylpiperazine, 20% to 1-(4-methoxyphenyl)piperazine, 10% to 1-(4-hydroxyphenyl)piperazine, 38% to 1-(4-fluorophenyl) piperazine, 156% to 1-(3-hydroxyphenyl)piperazine, 61% to 1-(3-trifluoromethylphenyl)piperazine, 34% to 1-(2-methoxyphenyl)piperazine; and less than 1% to each of 4-(4-chlorophenyl)-4-hydroxypiperidine, 1-benzylpiperazine, mephedrone, mescaline, (+)-pseudoephedrine, MDPBP, JWH-018, JWH-250, salvinorin A, piperazine, 1-methyl-3-phenylpiperazine, trazodone, MCPCP and 3-amino-2-hydroxybenzotrifluoride;
   wherein the cross reactivity is measured in the presence of a detecting agent, wherein the detecting agent is a conjugate of 1-(4-carboxymethyletherphenyl)piperazine linked through the carboxy group to horseradish peroxidase.

3. A method of detecting one or more piperazine derivatives comprising:
   contacting a sample with the polyclonal antibody of claim 1 and a detecting agent, wherein the detecting agent is a conjugate of 1-(4-carboxymethyletherphenyl)piperazine linked through the carboxy group to horseradish peroxidase; and
   detecting the detecting agent.

4. The method of claim 3, wherein the piperazine derivative is 1-(3-chlorophenyl)piperazine, 1-(3-methylphenyl)piperazine), 1-phenylpiperazine, 1-(4-methoxyphenyl)piperazine, 1-(4-hydroxyphenyl)piperazine, 1-(4-fluorophenyl)piperazine, 1-(3-hydroxyphenyl)piperazine, or 1-(3-trifluoromethylphenyl)piperazine.

5. A method of detecting one or more piperazine derivatives comprising:
   contacting a sample with the polyclonal antibody of claim 2 and a detecting agent, wherein the detecting agent is a conjugate of 1-(4-carboxymethyletherphenyl)piperazine linked through the carboxy group to horseradish peroxidase; and
   detecting the detecting agent.

6. The method of claim 5, wherein the piperazine derivative is 1-(3-chlorophenyl)piperazine, 1-(3-methylphenyl)piperazine), 1-phenylpiperazine, 1-(4-methoxyphenyl)piperazine, 1-(4-hydroxyphenyl)piperazine, 1-(4-fluorophenyl)piperazine, 1-(3-hydroxyphenyl)piperazine, 1-(3-trifluoromethylphenyl)piperazine; or 1-(2-methoxyphenyl)piperazine.

7. A method of detecting one or more piperazine derivatives comprising:
   contacting a sample with the polyclonal antibody of claim 1, the polyclonal antibody of claim 1, and a detecting agent, wherein the detecting agent is a conjugate of 1-(4-carboxymethyletherphenyl)piperazine linked through the carboxy group to horseradish peroxidase; and detecting the detecting agent.

8. The method of claim 7, wherein the piperazine derivative is 1-(3-chlorophenyl)piperazine, 1-(3-methylphenyl)piperazine), 1-phenylpiperazine, 1-(4-methoxyphenyl)piperazine, 1-(4-hydroxyphenyl)piperazine, 1-(4-fluorophenyl)piperazine, 1-(3-hydroxyphenyl)piperazine, 1-(3-trifluoromethylphenyl)piperazine; or 1-(2-methoxyphenyl)piperazine.

9. A kit comprising the polyclonal antibody of claim 1 and a detecting agent, wherein the detecting agent is a conjugate of 1-(4-carboxymethyletherphenyl)piperazine linked through the carboxy group to horseradish peroxidase.

10. A kit comprising the polyclonal antibody of claim 2 and a detecting agent, wherein the detecting agent is a conjugate of 1-(4-carboxymethyletherphenyl)piperazine linked through the carboxy group to horseradish peroxidase.

11. A kit comprising the polyclonal antibody of claim 1, the polyclonal antibody of claim 1, and a detecting agent, wherein the detecting agent is a conjugate of 1-(4-carboxymethyletherphenyl)piperazine linked through the carboxy group to horseradish peroxidase.

12. A method of making the polyclonal antibody of claim 1 comprising administering to a mammal an immunogen, wherein the immunogen is a conjugate of 1-(4-carboxymethyletherphenyl)piperazine linked through the carboxy group to bovine thyroglobulin.

13. A method of making the polyclonal antibody of claim 2 comprising administering to a mammal an immunogen, wherein the immunogen is a conjugate of 1-(3-carboxyphenyl)piperazine linked through the carboxy group to bovine thyroglobulin.

* * * * *

UNITED STATES PATENT AND TRADEMARK OFFICE
CERTIFICATE OF CORRECTION

PATENT NO. : 10,253,006 B2  
APPLICATION NO. : 15/130137  
DATED : April 9, 2019  
INVENTOR(S) : Elouard Benchikh et al.

Page 1 of 1

It is certified that error appears in the above-identified patent and that said Letters Patent is hereby corrected as shown below:

In the Claims

Claim 7, Column 16, Lines 64-65, the text "contacting a sample with the polyclonal antibody of claim 1, the polyclonal antibody of claim 1, and a detecting" should be changed to --contacting a sample with the polyclonal antibody of claim 1, the polyclonal antibody of claim 2, and a detecting--

Claim 11, Column 18, Lines 1-2, the text "11. A kit comprising the polyclonal antibody of claim 1, the polyclonal antibody of claim 1, and a detecting agent," should be changed to --11. A kit comprising the polyclonal antibody of claim 1, the polyclonal antibody of claim 2, and a detecting agent,--

Signed and Sealed this  
Twenty-fourth Day of September, 2019

Andrei Iancu  
*Director of the United States Patent and Trademark Office*